United States Patent [19]

Davie

[11] 4,159,275
[45] Jun. 26, 1979

[54] COLOR OF MALEIC ANHYDRIDE

[75] Inventor: William R. Davie, Hopewell Township, Beaver County, Pa.

[73] Assignee: United States Steel Corporation, Pittsburgh, Pa.

[21] Appl. No.: 925,088

[22] Filed: Jul. 17, 1978

[51] Int. Cl.² ............................................ C07D 307/60
[52] U.S. Cl. .................................................. 260/346.76
[58] Field of Search ....................... 260/346.74, 346.76

[56] References Cited

U.S. PATENT DOCUMENTS

| | | | |
|---|---|---|---|
| 3,115,477 | 12/1963 | Bowman et al. | 260/346.74 |
| 3,622,600 | 11/1971 | Feder | 260/346.74 |
| 3,775,436 | 11/1973 | Stenseth | 260/346.74 |

Primary Examiner—Natalie Trousof
Assistant Examiner—Bernard Dentz
Attorney, Agent, or Firm—William L. Krayer

[57] ABSTRACT

Discoloration of maleic anhydride is minimized by first passing the maleic anhydride in molten or dissolved form through a bed of cation exchange resin and then adding to the maleic anhydride a small amount of 3,3'-thiodipropionitrile.

3 Claims, No Drawings

COLOR OF MALEIC ANHYDRIDE

BACKGROUND OF THE INVENTION

A common problem in the manufacture of maleic anhydride is that it may exhibit a slight coloration from impurities in very small amounts. Even a slight color is highly undesirable for many uses of maleic anhydride, such as the manufacture of polyester resins. The specifications accepted by the industry for many purposes include an APHA color reading of less than 40 after heating for 24 hours at 140° C.

Prior to the present invention, it has been known to stabilize the color of maleic anhydride with certain sulfide compounds (U.S. Pat. No. 3,564,022), certain thiophosphates (U.S. Pat. No. 3,636,057), and certain chelating agents, such as EDTA (U.S. Pat. No. 3,115,503).

Thiodipropionitrile has been used to stabilize methylchloroform (U.S. Pat. No. 3,265,747), to inhibit polymerization of conjugated dienes (U.S. Pat. No. 3,523,141), and to stabilize polybutadiene (U.S. Pat. No. 3,355,421).

Thiodipropionic acid and its esters have been proposed for stabilizing maleic anhydride.

Color-stable maleic anhydride has also been disclosed as achievable by passing molten maleic anhydride through a bed of alkali sulfates or halides (U.S. Pat. No. 3,622,600).

None of the above methods has completely solved the problem. The industry is still looking for a consistent method of assuring stability of clear color in maleic anhydride.

I have studied the maleic heat-color problem and found that it may be caused by two factors, (1) alkali metal cations or tertiary amines and/or (2) oxidation. For example, maleic anhydride is so sensitive to alkali metal ions that heat-color tests cannot be run in soft glass tubes. The small amount of sodium ions present in soft glass is enough to severely darken maleic anhydride in the 24-hour heat-color test. Maleic anhydride is also very sensitive to tertiary amines. Less than 10 parts per billion nitrogen as pyridine can produce an unacceptable 24-hour heat color. I have found that these harmful substances can readily be removed by passing the molten maleic anhydride through an anhydrous acidic cation-exchange resin. For this treatment, I prefer "Amberlyst 15", manufactured by Rohm and Haas Co. It has a "macroreticular" structure which is highly porous, and in contrast to conventional ion exchange resins, it does not lose its porosity when the swelling solvent, water, is removed. The resin is made from a sulfonated styrene divinylbenzene copolymer. Although the anhydrous resin can be used without treatment, I prefer to wash it first with a suitable solvent (hot methanol is preferred) to remove superfluous low-molecular-weight sulfonated materials because these substances can contribute to high heat color. After washing, the resin is dried and the molten maleic anhydride may be passed over it, i.e., through a bed or column. The resin-column temperatures may range from slightly above the melting point of maleic anhydride to 100° C. Contact times may be from about 1 minute to about 15 minutes. The longer contact times and higher temperatures are generally not as efficient as the shorter contact times and lower temperatures, because higher temperatures and longer contact times apparently leach minute amounts of undesirable materials from the cation-exchange resin and result in high heat colors. I prefer to use about 70° C. and about 2 to 10 minute contact time with the resin. At lower temperatures, longer contact time is required but at higher temperatures shorter contact time should be used. Below the melting point of maleic anhydride (52.5 C), a solvent may be used to keep the maleic anhydride in a liquid form for treatment with the cation-exchange resin if such a procedure is to be used.

Among the solvents which may be used are xylenes and other aromatic hydrocarbons that are unreactive toward maleic anhydride.

The 24-hour heat color of maleic anhydride samples originally containing large amounts of basic material has been significantly improved by treatment with only the cation-exchange resin. Other samples of maleic anhydride containing oxidizable materials as the main impurity were only slightly improved after cation-exchange treatment. But, treatment with 3,3'-thiodipropionitrile significantly improved these latter samples.

Since most newly-manufactured maleic anhydride apparently contains some of both types of impurities, the combined treatment, cation-exchange resin followed by antioxidant, yields better heat colors than either treatment separately.

In the screening of chemicals and antioxidants, it was found that many conventional chemicals normally considered to be good antioxidants were ineffective and in some cases even detrimental to the 24-hour heat color.

Antioxidants or reducing agents that improved maleic anhydride heat color were:
1. Paraformaldehyde and formaldehyde derivatives such as methylal
2. Aluminum metal
3. Dimyristyl thiodipropionate and thiodipropionic acid
4. 3,3'-Thiodipropionitrile
5. 2,5-Dihydrothiophene-1,1-dioxide
6. o-Phenyl phenol
7. 4,4'-Sulfonyl diphenol
8. O-Hydroxyacetophenone
9. Di-n-butyl carbonate
10. Zinc metal 3,3'-Thiodipropionitrile is the antioxidant I employ in my invention. It was evaluated and found to be quite effective over the range from 100 to 2,000 parts per million (ppm). It would not be practical to use it at rates over 2,000 ppm. It was still very effective at 100 ppm, is beneficial at concentrations as low as 10 ppm, and effective in proportionately lesser degrees in amounts less than 10 ppm, to as little as 1 ppm.

By far the most effective treatment, however, is the combined treatment of maleic anhydride using the strongly acidic cation-exchange resin and the addition of 3,3'-thiodipropionitrile to the maleic anhydride.

The effects of various treatments of maleic anhydride may be seen in the following Tables I–VII.

In each case, the addition of the antioxidant was accomplished by directly adding the antioxidant to molten maleic anhydride. The residence time in the column was set by the flow rate through the column. The color test used was a standard 24-hour test at 140° C. in "Pyrex" color tubes.

While I prefer to use "Amberlyst 15" as the acidic cation-exchange resin, I may employ any cation-exchange resin in the acidic form; preferably the resin will be one which is readily dried and does not unduly shrink or crack in the absence of water. Another cation-exchange resin which may be used in the acidic form is Dowex MSC-1.

Solvents which may be used in the column are xylenes and other aromatic hydrocarbons that are inert to maleic anhydride.

TABLE I

Effect of Pyridine on Maleic Anhydride Heat Color

| Heat Color | 24 hr, 140° C. Heat Color |
|---|---|
| 1. Untreated control (very good maleic anhydride) | APHA 60 |
| 2. Control + 0.04 ppm pyridine (7 ppb nitrogen) | APHA 150 |
| 3. Control + 0.55 ppm pyridine (0.1 ppm nitrogen) | APHA >500 |
| 4. Control + 2.7 ppm pyridine (0.5 ppm nitrogen) | Brown |

TABLE II

Effect of Column Treatment Only on Maleic Anhydride

| Heat Color | 24 hr, 140° C. Heat Color |
|---|---|
| 5. Untreated control (poor quality apparently containing basic impurities) | APHA >500 |
| 6. Control put through Amberlyst 15 columns then heat treated | APHA 60 |
| 7. Sample identical to #4 above put through column then heat treated | APHA 75 |

TABLE III

Effect of Column Residence Time at 70° C. on Maleic Anhydride Heat Color

| Heat Color | 24 hr, 140° C. Heat Color |
|---|---|
| 8. Untreated control (good maleic anhydride) | APHA 65 |
| 9. 2 minutes residence time in column | APHA 60 |
| 10. 4 minutes residence time | APHA 60 |
| 11. 10 minutes | APHA 50 |
| 12. 15 minutes | APHA 70 |

TABLE IV

Effect of Column Temperature on Maleic Anhydride Heat Color at 5 Minutes Residence Time in Column

| | Heat Color | 24 hr, 140° C. Heat Color |
|---|---|---|
| 13. | 60° C. column temperature | APHA 75 |
| 14. | 70° C. | APHA 70 |
| 15. | 80° C. | APHA 80 |
| 16. | 90° C. | APHA 150 |

TABLE V

Effect of Antioxidant Treatments Alone on Maleic Anhydride Heat Color (1000 ppm Antioxidants)

| Heat Color | 24 hr, 140° C. Heat Color |
|---|---|
| 17. Untreated control (fair quality) | APHA 125 |
| 18. Paraformaldehyde | APHA 100 |
| 19. Zinc metal | APHA 100 |
| 20. Dimyristyl thiodipropionate | APHA 75 |
| 21. Methylal | APHA 80 |
| 22. 3,3'-Thiodipropionitrile | APHA 50 |
| 23. o-Phenylphenol | APHA 100 |
| 24. Aluminum metal | APHA 100 |
| 25. 2,5-Dihydrothiophene-1,1-dioxide | APHA 75 |

TABLE V-continued

Effect of Antioxidant Treatments Alone on Maleic Anhydride Heat Color (1000 ppm Antioxidants)

| Heat Color | 24 hr, 140° C. Heat Color |
|---|---|
| 26. 4,4'-Sulfonyl diphenol | APHA 85 |
| 27. o-Hydroxyacetophenone | APHA 85 |
| 28. Di-n-butyl carbonate | APHA 90 |
| 29. Thiodipropionic acid | APHA 70 |

TABLE VI

Effect of Antioxidant Only on Maleic Anhydride that Contains Pyridine (Note that in test #7 the ion exchange column was able to remove pyridine and give good heat color)

| Heat Color | 24 hr, 140° C. Heat Color |
|---|---|
| 30. Control + 2.7 ppm pyridine treated with dimyristyl thiodipropionate before heat treatment | Brown |

TABLE VII

Combination Column and Antioxidant Treatment of Maleic Anhydride Versus Single Treatments

| Heat Color | 24 hr, 140° C. Heat Color |
|---|---|
| 31. Untreated control A (poor quality due to oxidizable impurities) | APHA >500 |
| 32. Column treatment only | APHA 500 |
| 33. Antioxidant treatment only (dimyristyl thiodipropionate) 200 ppm | APHA 65 |
| 34. Antioxidant treatment only (3,3'-thiodipropionitrile) 200 ppm | APHA 60 |
| 35. Column + antioxidant (dimyristyl) thiodipropionate) 200 ppm | APHA 40 |
| 36. Column + antioxidant (3,3'-thiodipropionitrile) 200 ppm | APHA 40 |
| 37. Untreated control B (good quality apparently contaning very little basic impurities) | APHA 90 |
| 38. Column treatment only | APHA 125* |
| 39. Column + antioxidant (3,3'-thiodipropionitrile) 200 ppm | APHA 30* |
| 40. Antioxidant only (3,3'-thiodipropionitrile) 200 ppm | APHA 50* |
| 41. Untreated control C | APHA >500 |
| 42. Column treatment only | APHA 300 |
| 43. Column + 150 ppm 3,3'-thiodipropionitrile | APHA <20 |
| 44. Untreated control D (good quality with oxidizable materials as main impurities) | APHA 100 |
| 45. 1000 ppm 3,3'-thiodipropionitrile added | APHA 50 |
| 46. 500 ppm 3,3'-thiodipropionitrile added | APHA 50 |
| 47. 200 ppm 3,3'-thiodipropionitrile added | APHA 50 |
| 48. 100 ppm 3,3'-thiodipropionitrile added | APHA 50 |

*Column treatment alone was slightly detrimental yet combined treatment was better than individual treatments.

I claim:

1. Method of treating maleic anhydride to remove color therefrom comprising passing molten or dissolved maleic anhydride through an acidic cation-exchange column to remove cations therefrom, and thereafter adding to the maleic anhydride thus treated from about 1 to about 1000 ppm of 3,3'-thiodipropionitrile.

2. Method of claim 1 wherein the maleic anhydride is dissolved in xylene when it is passed through the ion-exchange column.

3. Method of claim 1 wherein residence time of the maleic anhydride in the ion-exchange column is about 1 minute to about 15 minutes.